(12) United States Patent
Chatellier

(10) Patent No.: US 6,948,370 B2
(45) Date of Patent: Sep. 27, 2005

(54) METHOD OF MEASURING THE ADHESION OF A COATING TO A SUBSTRATE

(75) Inventor: Jean-Yves Chatellier, Arcueil (FR)

(73) Assignee: SNECMA Moteurs, Paris (FR)

( * ) Notice: Subject to any disclaimer, the term of this patent is extended or adjusted under 35 U.S.C. 154(b) by 0 days.

(21) Appl. No.: 11/041,997

(22) Filed: Jan. 26, 2005

(65) Prior Publication Data
US 2005/0186328 A1 Aug. 25, 2005

(30) Foreign Application Priority Data
Feb. 5, 2004 (FR) .................................. 04 01085

(51) Int. Cl.[7] .................. G01N 29/02; G01N 29/04; G01N 9/24
(52) U.S. Cl. ............................ 73/600; 427/8
(58) Field of Search .................. 73/600, 599, 602, 73/646, 579, 627, 629; 427/8

(56) References Cited

U.S. PATENT DOCUMENTS

| | | | |
|---|---|---|---|
| 4,541,287 A | * | 9/1985 | Roper ........................ 73/827 |
| 5,359,899 A | * | 11/1994 | Nishimura et al. ........... 73/842 |
| 5,537,884 A | * | 7/1996 | Nishimura et al. ........... 73/842 |
| 5,663,502 A | * | 9/1997 | Nagashima et al. .......... 73/599 |
| 5,698,790 A | * | 12/1997 | Nishimura et al. ........... 73/842 |
| 6,070,473 A | | 6/2000 | Nishimura et al. |
| 6,314,819 B1 | * | 11/2001 | Nishimura et al. ........... 73/842 |
| 6,684,703 B2 | | 2/2004 | Chatellier et al. |
| 2002/0162395 A1 | | 11/2002 | Chatellier et al. |

FOREIGN PATENT DOCUMENTS

| | | |
|---|---|---|
| DE | 100 04 212 C1 | 7/2001 |
| EP | 1 130 391 A1 | 9/2001 |
| JP | 63-175762 | 7/1988 |
| RU | 1698746 A1 | 12/1991 |

* cited by examiner

*Primary Examiner*—Edward Lefkowitz
(74) *Attorney, Agent, or Firm*—Oblon, Spivak, McClelland, Maier & Neustadt, P.C.

(57) ABSTRACT

A method of measuring the adhesion of a coating to a substrate, wherein the measurement is done in air and wherein an ultrasound transducer is applied to the substrate by means of a thin film of gel, and a quality factor is calculated, given by the ratio between the amplitudes of the echoes associated with the first two reflections on the substrate/coating interface after passing through the substrate or on the coating/air interface after passing through the substrate and the coating.

8 Claims, 3 Drawing Sheets

METHOD OF MEASURING THE ADHESION OF A COATING TO A SUBSTRATE

BACKGROUND OF THE INVENTION

The present invention relates to a method of measuring the adhesion of a coating to a substrate, and in particular of a metallic coating deposited on a metallic substrate.

The adhesion of a coating to a substrate can be assessed using test pieces made up of disks of the same material as the substrate with the coating on one of their sides. These disks are bonded onto counter-test pieces that are fixed to the jaws of a tensile testing machine. The measurement of the adhesion of the coating is then supplied by a mechanical measurement of the force needed to tear the coating from the substrate.

However, considerable discrepancies in the tensile strength measured on identical test pieces are observed, which shows that the method used introduces uncertainties which are great enough for it to be difficult to attach any value to these tests. It is probable that the bonding is responsible for defects of uniformity of transmission of the tensile force through the assembly but this cannot be remedied even by taking the greatest care in creating the bond.

Furthermore, with certain tungsten carbide type coatings which offer an adhesion greater than that of the bonding agent used, these tests measure the tensile strength of the bond and not that of the coating.

DESCRIPTION OF THE PRIOR ART

The applicant's patent EP 1 130 391 describes a method of measuring the adhesion of a coating to a substrate using ultrasound waves, this method using a transducer separate from the sample to be measured and immersed with the sample in a tank filled with water.

This known method can be applied only to test pieces because it is normally not possible to immerse an actual large piece in a water-filled tank. Nor can it be applied to porous coatings which absorb the water from the tank by capillary action, rendering the measurement ineffective.

Furthermore, in this known method, it is essential for the transducer to be oriented at right angles to the test piece to be measured, with any deviation from this orthogonal alignment causing wave dispersions in the water and distorting the measurements.

SUMMARY OF THE INVENTION

One object of the present invention is to overcome these problems, through a method that can be used in particular to obtain an in-situ evaluation of the adhesion of a coating of a substrate or of any part, using ultrasound waves.

This object is achieved through a method of measuring the adhesion of a coating to a substrate, consisting in sending ultrasound waves by means of a transducer toward the substrate and the coating, picking up a series of echoes resulting from reflections of the ultrasound waves on the surfaces of the substrate and of the coating, and calculating an amplitude, ratio of two successive echoes, wherein the measurement is done in air and wherein the method also consists in applying the transducer to the substrate by means of a thin film of gel, calculating a coating quality factor given by the ratio between the amplitudes of the echoes associated with the first two reflections on the substrate/coating interface after passing through the substrate or on the coating/air interface after passing through the substrate and the coating, and in determining the adhesion of the coating from a correlation function between the quality factor and the breaking stress of the coating, obtained previously by mechanical tests on calibration test pieces.

The method as claimed in the invention can be applied to all types of parts and coatings. In particular, it can be used to take in-situ measurements on any coated parts and on porous coatings.

When the acoustic impedance of the substrate is high compared to that of the coating, the ultrasound wave is reflected by the substrate-coating interface. When the acoustic impedances of the substrate and of the coating are similar, the ultrasound wave passes through this interface and the coating and is reflected by the coating-air interface.

The method as claimed in the invention can be used to repeat the in-situ measurements at regular or irregular time intervals to monitor the trend of the quality of the adhesion of the coating to a part over time.

Another advantage of the method as claimed in the invention is the determination of the quality of the substrate-coating bond and the quality of the coating structure.

In general, a major advantage of the present invention is that it allows rapid in-situ measurements on coated parts, without dismantling and without immersing these parts.

BRIEF DESCRIPTION OF THE DRAWINGS

Other benefits and features of the invention will become apparent on reading the description below, given by way of nonlimiting example and with reference to the appended drawings in which.

DESCRIPTION OF THE PREFERRED EMBODIMENTS

Figure 1:
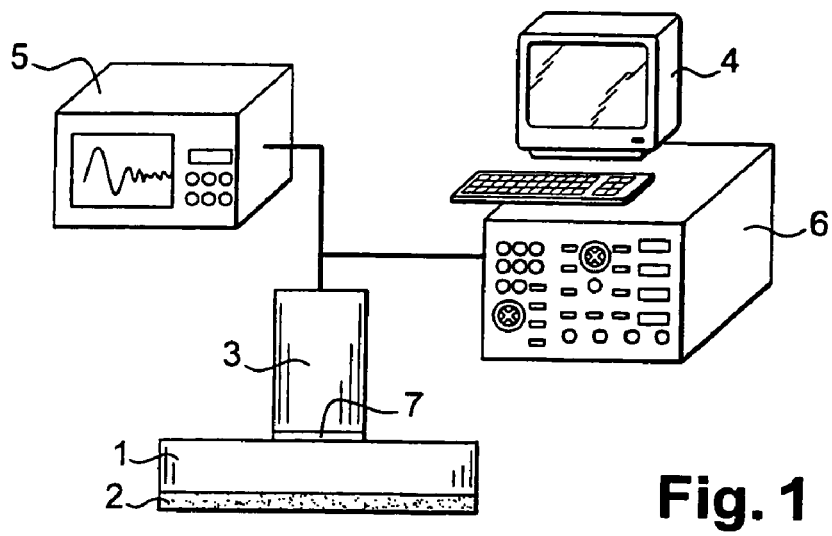
FIG. 1 is a diagrammatic view of the apparatus used to carry out the method as claimed in the invention.

In FIG. 1, the reference 1 designates a substrate, formed by any material, and the reference 2 designates a coating deposited on this substrate. Typically, the substrate and the coating are metallic.

The coating 2 has been produced by a method such as plasma spraying for which the adhesion measurements have a great importance because of the structural irregularity of the coating 2 and therefore of its fragility. The coating 2 is very much thinner than the substrate 1.

A transducer 3 generating a longitudinal ultrasound wave is applied to the substrate on the side opposite to the coating 2. The transducer 3 is linked to a control means 4, such as a microcomputer, to an oscilloscope 5 and to a pulse generator 6.

To improve the contact between the transducer and the surface to which it is applied, a thin film 7 of gel is placed between them, with a thickness of approximately 10 $\mu$m.

The transducer 3 sends a longitudinal ultrasound wave and also functions as a receiver. The oscilloscope 5 records and displays the echoes picked up by the transducer 3 and is used to analyze them as described below.

Figure 2:
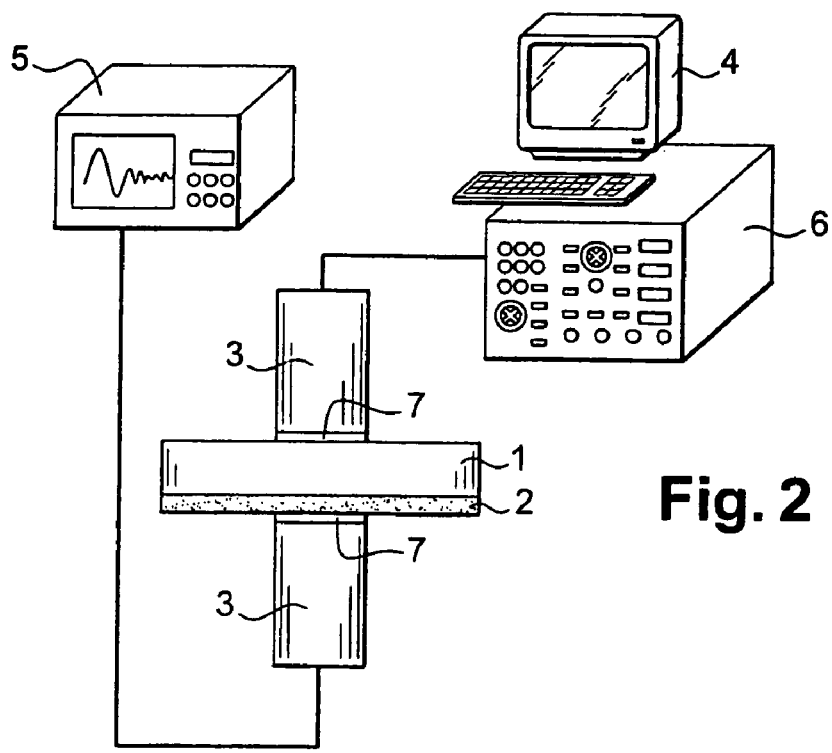
FIG. 2 is a diagrammatic view of the apparatus used according to an embodiment of the invention.

FIG. 2 illustrates a variant of the apparatus, in which two transducers 3, 3' are used. The first transducer 3 is positioned in the same way as described previously and is designed to send ultrasound waves while the second transducer 3', in contact with the free bottom surface of the coating 2, functions as a receiver, the first transducer 3 being linked to the control means 4 and to the pulse generator 6, the second transducer 3' being linked to the oscilloscope 5.

In this variant, the measurement is performed not on the reflections of the ultrasound wave, but on the transmissions through the coating 2.

When the acoustic impedances of the substrate 1 and of the coating 2 are significantly different, the ultrasound wave generated by the transducer 3 is reflected at the substrate 1/coating 2 interface, whereas, conversely, if the acoustic impedances are similar, the ultrasound wave generated by the transducer 3 passes through the coating 2 and is reflected at the coating 2/air interface.

Figure 3:
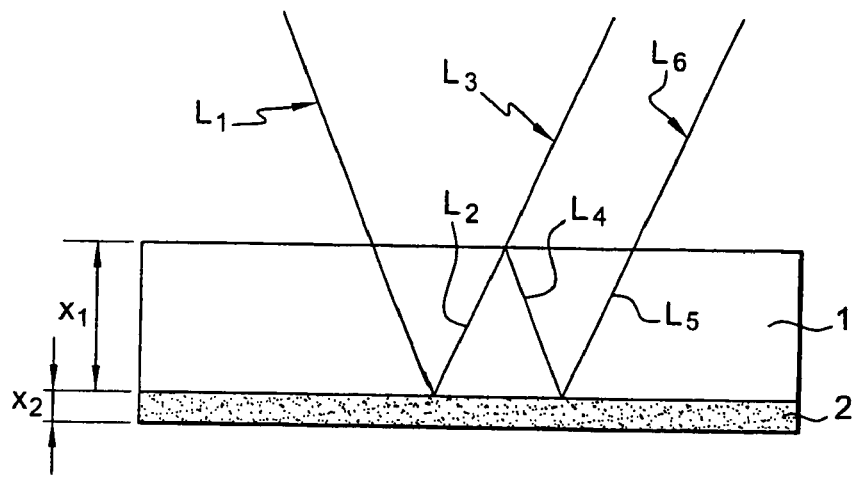
FIGS. 3 and 4 are diagrammatic views illustrating two ultrasound reflection modes.
Figure 4:
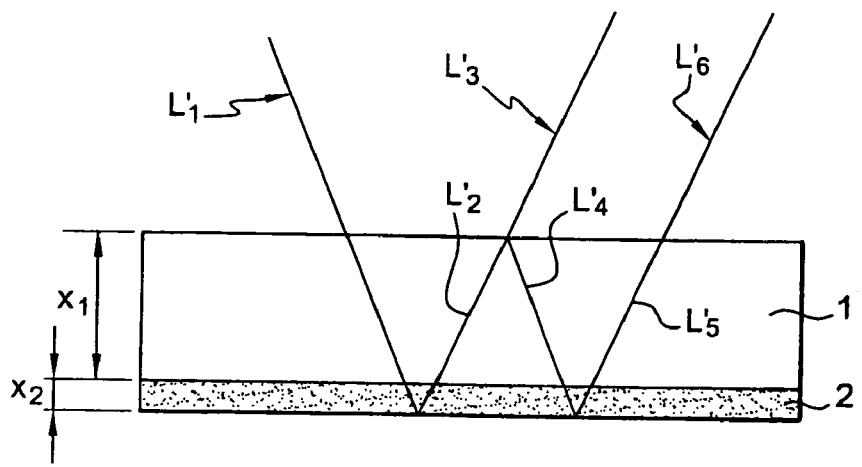

FIGS. 3 and 4 illustrate the corresponding reflection modes of the ultrasound waves by the abovementioned interfaces, the direction of the wave being shown diagonally for greater clarity. The ultrasound waves sent and received are in reality directed perpendicularly to the top surface of the substrate 1, the diagonal representation being designed to simplify the drawing and simplify the explanation, with the measurement principle being unchanged.

In FIG. 3, the wave sent by the transducer 3 applied to the surface of the substrate 1 is represented by the line $L_1$. Since the contact is provided by a very thin film 7 of gel, the part of the wave reflected by the top surface of the substrate 1 is undetectable.

Since the acoustic impedances of the substrate 1 and the coating 2 are different, the ultrasound wave transmitted through the substrate 1 is reflected at the substrate 1/coating 2 interface along a line $L_2$.

The ultrasound wave which passes through the substrate along the line $L_2$ is partly transmitted to the outside along the line $L_3$ and forms a "first echo", and partly reflected at the substrate 1/air interface and passes back through the substrate 1 along the line $L_4$ to be partly reflected again along the line $L_5$, at the substrate 1/coating 2 interface. The ultrasound wave propagating along the line $L_5$ is partly transmitted to the outside through the substrate 1/air interface along the line $L_6$ and forms a "second echo".

In FIG. 4, the acoustic impedances of the substrate 1 and the coating 2 are not very different and the wave transmitted by the transducer 3 along $L_1'$ passes through the substrate 1 and the coating 2 and is reflected along the line $L_2'$, by the coating 2/air interface.

The wave reflected along the line $L_2'$ is partly transmitted ("first echo") and partly reflected along the lines $L_3'$ and $L_4'$, respectively, as described previously. The wave reflected along $L_4'$ is again partly reflected by the coating 2/air interface along the line $L_5'$. A part of this reflected wave is transmitted along the line $L_6'$ through the substrate 1/air interface and forms the "second echo".

The lines $L_2$, $L_4$, $L_5$ and $L_2'$, $L_4'$, $L_5'$ passing through the substrate 1 have the same length, even though the successive echoes arriving at the transducer 3 along the lines $L_3$, $L_6$ and $L_3'$, $L_6'$ are separated by equal time intervals, respectively corresponding to twice the transit time of the ultrasound waves through the thickness $x_1$ of the substrate 1, and through the thickness $x_1+x_2$ of the substrate 1 and of the coating 2.

Figure 5:
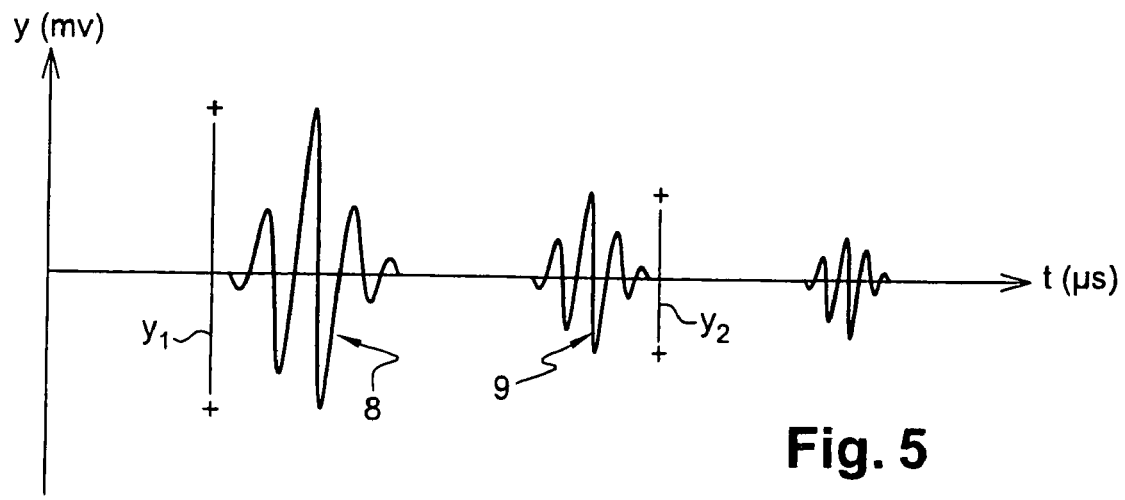
FIG. 5 represents an echo curve obtained by the method.

The method as claimed in the invention consists in measuring the amplitudes of the first two successive echoes of the wave transmitted by the transducer 3, these two echoes being designated by the references 8 and 9 in the diagram of FIG. 5 which represents the trend of the amplitude of the echoes over time.

The quality factor of the coating is defined as the ratio of the amplitudes $y_1$ and $Y_2$ of the first two echoes.

For a part for which the acoustic impedances of the substrate and of the coating are similar, in other words for a reflection at the coating 2/air interface, the quality factor of the coating is expressed as:

$$Q = \frac{y_1}{y_2} = \frac{e^{2\alpha_1 x_1}}{r_{1cc}} \cdot \frac{e^{2\alpha_2 x_2}}{t_{12} t_{21}}$$

For a part for which the acoustic impedances of the substrate 1 and of the coating 2 are significantly different, in other words for a reflection at the substrate 1/coating 2 interface, the quality factor of the coating is expressed as:

$$Q' = \frac{y_1'}{y_2'} = \frac{e^{2\alpha_1 x_1}}{r_{1cc}} \cdot \frac{1}{r_{12}}$$

In these expressions, $\alpha_1$ and $\alpha_2$ are the attenuation coefficients of the ultrasound waves in the substrate 1 and in the coating 2, respectively, $t_{12}$ and $t_{21}$ are the amplitude transmission coefficients from the substrate 1 to the coating 2 and from the coating 2 to the substrate 1, respectively, and $r_{1cc}$, and $r_{12}$ are the amplitude-wise reflection coefficients at the substrate 1/thin film 7 interface and at the substrate 1/coating 2 interface, respectively.

The quality factor Q comprises a first term which involves the properties of the substrate 1, and a second term which involves the structural quality of the coating 2 through the quantity $e^{2\alpha_2 x_2}$ and the quality of its bond with the substrate 1 through the quantity $t_{12} t_{21}$.

Similarly, the quality factor Q' comprises a first term which involves the properties of the substrate 1, and a second term which involves the quality of the bond of the coating 2 with the substrate 1 through the coefficient $r_{12}$.

It has been observed that the reflection coefficient $r_{1cc}$ between the substrate 1 and the thin film 7 of gel is equal to the reflection coefficient between the substrate 1 and water, and that it can be determined experimentally. This means that the properties of the material used to form the thin film 7 can be disregarded in calculating the quality factor.

A correlation is established between the quality factor and the adhesion of the coating 2 by means of mechanical measurements on calibration test pieces, which are carried out as follows.

Figure 6:
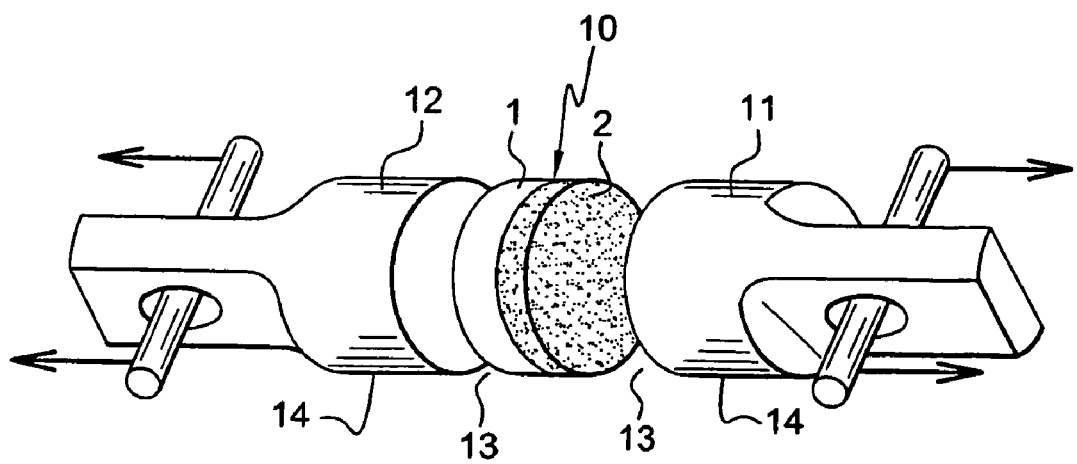
FIG. 6 is a diagrammatic view illustrating a mechanical tensile strength test.

These test pieces are disks of the same type as the parts to be coated, having, for example, a diameter of one inch (25.4 millimeters) and a thickness of six millimeters, which are placed beside the parts to be coated and receive the same coating 2 as these parts. Then, as is diagrammatically represented in FIG. 6, each disk 10 is bonded to two counter-test pieces 11, 12 using a high strength adhesive 13 such as FM1000 from American Cyanamid. The two counter-test pieces are fixed in the jaws or gripping heads 14 of a tensile testing machine. The loading rate of the disk 10 is constant, for example 0.8 MPa/s, which corresponds to a displacement of one millimeter per minute.

The adhesion of the coating 2 to the substrate 1 is measured as the force needed to separate it from the substrate 1. The breaking stress a is the ratio of the maximum tensile force reached to the area of the surface on which the coating 2 is deposited.

Figure 7:
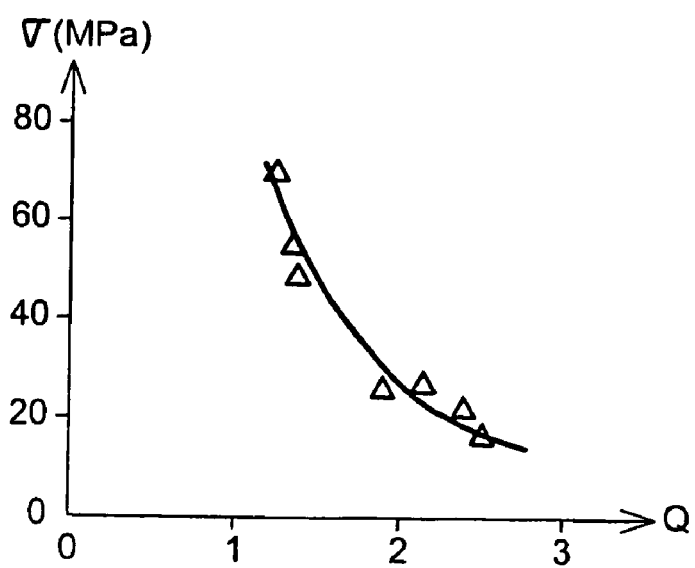
FIG. 7 represents a correlation curve between the breaking stress and the quality factor.

FIG. 7 represents a curve showing the variation of the breaking stress σ in MPa versus the quality factor Q measured at a frequency of 5 MHz in the case of a 17% WC coating 2 on a Z12C13 substrate 1. It can be seen that, in this case, the quality factor Q increases when σ decreases.

In other cases, such as, for example, that of a 5% NiAl coating on a Z12C13 substrate, the quality factor Q' measured at a frequency of 10 MHz varies in the same direction as the breaking stress a and increases when the adhesion of the coating 2 to the substrate 1 is greater.

It is therefore possible, for each type of coating 2 and substrate 1, to establish a quality factor Q or Q' calibration curve from tensile tests performed on test pieces, then directly measure the quality factor Q or Q' on coated parts, so enabling the adhesion quality of the coating 2 to a part in situ to be established in a few minutes. Thus, the quality of the coating 2 can be checked, and its trend over time can be monitored, since the quality factor measurements can be repeated at predefined time intervals. The variability of the measurements of the quality factors is low compared to that of the tensile tests and these measurements fairly faithfully represent the adhesion of the coating.

Moreover, the invention can be used to evaluate the quality of the adhesion of a porous coating and that of coatings which have breaking stresss greater than that of the adhesive used to bond the test pieces in the tensile tests.

What is claimed is:

1. A method of measuring the adhesion of a coating to a substrate, consisting in sending ultrasound waves by means of a transducer toward the substrate and the coating, picking up a series of echoes resulting from reflections of the ultrasound waves on the surfaces of the substrate and of the coating, and calculating an amplitude ratio of two successive echoes, wherein the measurement is done in air and wherein the method also consists in applying the transducer to the substrate by means of a thin film of gel, calculating a coating quality factor given by the ratio between the amplitudes of the echoes associated with the first two reflections on the substrate/coating interface after passing through the substrate or on the coating/air interface after passing through the substrate and the coating, and in determining the adhesion of the coating from a correlation function between the quality factor and the breaking stress of the coating, obtained previously by mechanical tests on calibration test pieces.

2. The method as claimed in claim 1, wherein the ultrasound waves have a frequency of approximately 5 to 10 megahertz.

3. The method as claimed in claim 1, wherein the quality factor measurements are carried out in situ on coated parts.

4. The method as claimed in claim 3, which consists in repeating the measurements on the parts at regular or irregular time intervals to monitor the trend of the quality of the adhesion of the coating to the parts over time.

5. The method as claimed in claim 1, wherein the coating and the substrate are metallic.

6. The method as claimed in claim 1, wherein the thin film of gel has a thickness of approximately 10 μm.

7. The method as claimed in claim 1, wherein the quality factor of the coating given by the ratio between the amplitudes of the echoes associated with the first two reflections on the substrate/coating interface after passing through the substrate is expressed as:

$$Q' = \frac{e^{2\alpha_1 x_1}}{r_{1cc}} \cdot \frac{1}{r_{12}}$$

in which $\alpha_1$ is the attenuation coefficient of the ultrasound waves in the substrate, $x_1$ is the thickness of the substrate, and $r_{1cc}$ and $r_{12}$ are amplitude-wise reflection coefficients at the substrate/thin film interface and at the substrate/coating interface, respectively.

8. The method as claimed in claim 1, wherein the quality factor of the coating given by the ratio between the amplitudes of the echoes associated with the first two reflections on the coating/air interface after passing through the substrate and the coating is expressed as:

$$Q = \frac{e^{2\alpha_1 x_1}}{r_{1cc}} \cdot \frac{e^{2\alpha_2 x_2}}{t_{12} t_{21}}$$

in which $\alpha_1$ and $\alpha_2$ are the attenuation coefficients of the ultrasound waves in the substrate and in the coating, respectively, $x_1$ and $x_2$ are the thicknesses of the substrate and of the coating, respectively, $t_{12}$ and $t_{21}$ are the amplitude transmission coefficients from the substrate to the coating and from the coating to the substrate, respectively, and $r_{1cc}$ is the amplitude-wise reflection coefficient at the substrate/thin film interface.

* * * * *

UNITED STATES PATENT AND TRADEMARK OFFICE
CERTIFICATE OF CORRECTION

PATENT NO. : 6,948,370 B2  Page 1 of 1
DATED : September 27, 2005
INVENTOR(S) : Jean-Yves Chatellier It is certified that error appears in the above-identified patent and that said Letters Patent is hereby corrected as shown below:

Column 5,
Lines 1 and 12, change "a" to -- $\sigma$ --.

Signed and Sealed this

Fourteenth Day of February, 2006

JON W. DUDAS
*Director of the United States Patent and Trademark Office*